(12) United States Patent
Holshouser et al.

(10) Patent No.: US 8,500,679 B2
(45) Date of Patent: Aug. 6, 2013

(54) HUGGABLE BREASTPUMP

(75) Inventors: Kathryn Holshouser, Woodstock, IL (US); Jill M. Hunt, Woodstock, IL (US)

(73) Assignee: Medela Holding AG, Baar (CH)

( * ) Notice: Subject to any disclaimer, the term of this patent is extended or adjusted under 35 U.S.C. 154(b) by 52 days.

(21) Appl. No.: 13/152,669

(22) Filed: Jun. 3, 2011

(65) Prior Publication Data

US 2011/0301533 A1 Dec. 8, 2011

Related U.S. Application Data

(60) Provisional application No. 61/351,710, filed on Jun. 4, 2010.

(51) Int. Cl.
*A61M 1/06* (2006.01)
(52) U.S. Cl.
USPC .......................................................... 604/74

(58) Field of Classification Search
USPC .................... 604/74, 131, 151; 128/DIG. 12, 128/DIG. 13
See application file for complete search history.

(56) References Cited

U.S. PATENT DOCUMENTS

| | | | | |
|---|---|---|---|---|
| 5,954,690 A | * | 9/1999 | Larsson | 604/74 |
| 6,004,186 A | * | 12/1999 | Penny | 450/36 |
| 7,094,217 B2 | * | 8/2006 | Fialkoff | 604/74 |
| 7,611,399 B2 | * | 11/2009 | Brigham | 450/36 |
| 2003/0167037 A1 | * | 9/2003 | Fialkoff | 604/74 |
| 2003/0191433 A1 | * | 10/2003 | Prentiss | 604/74 |
| 2006/0270973 A1 | * | 11/2006 | Chu | 604/74 |

* cited by examiner

*Primary Examiner* — Manuel Mendez
(74) *Attorney, Agent, or Firm* — McDonnell Boehnen Hulbert & Berghoff LLP

(57) ABSTRACT

A soft carrier for a breastpump is disclosed. The carrier includes a cushion made of a soft, malleable outer material, for at least partially enclosing a breastpump and associated accessories. One or more breast shields extend outwardly from holes in the cushion. The soft carrier provides a more comfortable experience for the mother during pumping.

22 Claims, 17 Drawing Sheets

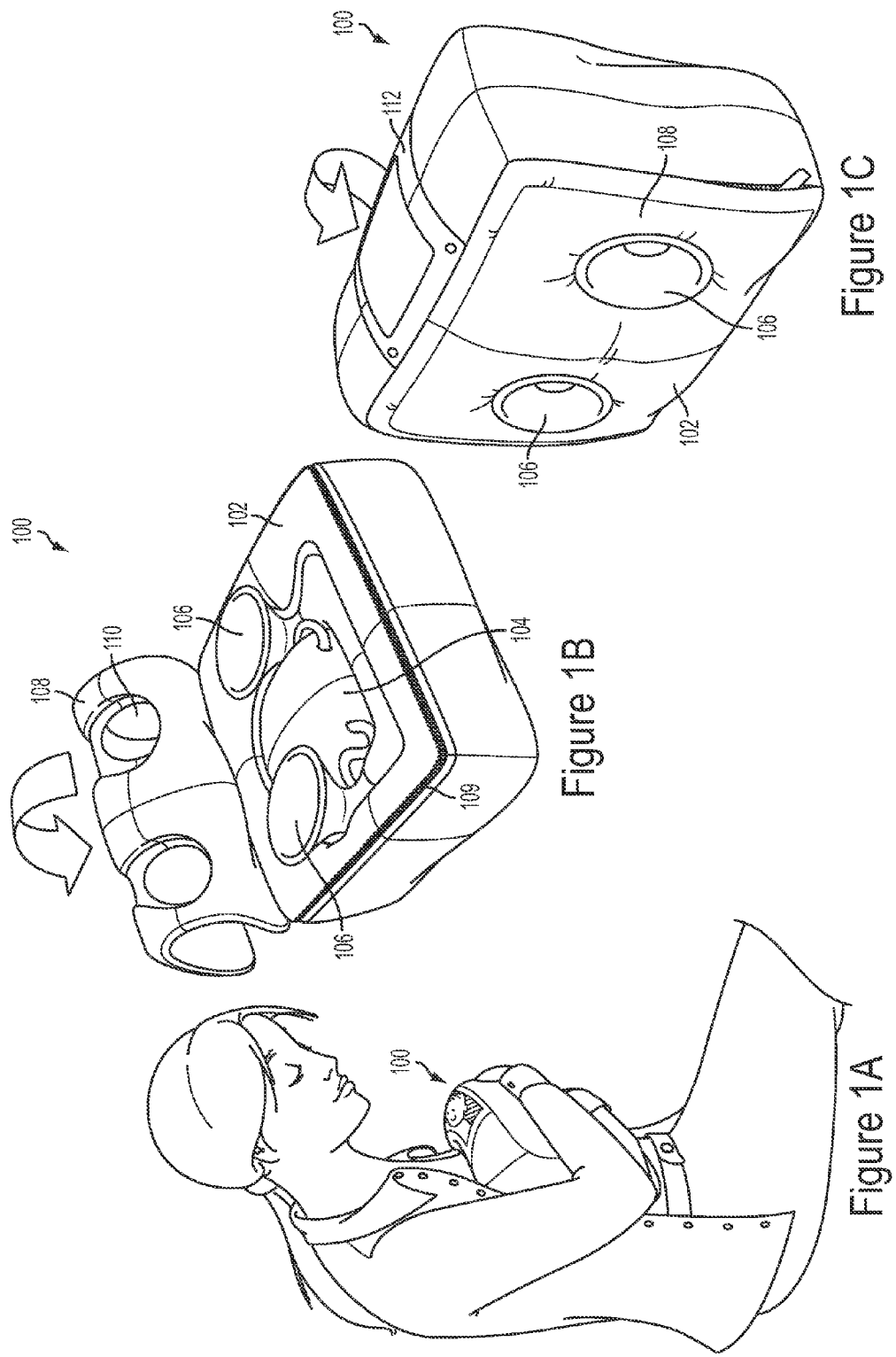

HUGGABLE BREASTPUMP

CROSS REFERENCE TO RELATED APPLICATIONS

This application claims priority to U.S. provisional application Ser. No. 61/351,710 filed on Jun. 4, 2010, the contents of which are fully incorporated by reference herein.

FIELD OF THE INVENTION

This invention relates to breastpumps for drawing breastmilk, and particularly to a breastpump which is huggable or embraceable by the mother.

BACKGROUND OF THE INVENTION

Breastpumps are traditionally provided in hard cases or housings, with a number of mechanical parts. Even the breast shield assemblies themselves, which a mother applies to her breast, tend to be hard plastic components. It is often difficult for the mother to carry around all of this equipment. It would therefore be desirable to consolidate much of the equipment into something easily held, and even to provide a comfortable breastpump package for a mother that is much more reminiscent of a suckling baby, or at least provides a "softer" experience.

SUMMARY OF THE INVENTION

The invention in a broad sense relates to a breastpump hidden or otherwise contained within a soft pliable article, case, cushion, pillow or like construct (collectively being generally referred to herein as a "cushion"). Conceptually, the invention provides a more comfortable experience for the mother, and perhaps also an easier pumping experience with the pumping equipment neatly arranged in a tidy package for use. Comfort is increased because the mother has something soft, and non-mechanical feeling and looking, which she can hold and embrace, as if hugging a baby. The cushion further serves to cover the mother's chest, much like a nursing baby would do so, keeping her warm and less "undressed." In essence, the experience is much more like nursing than milk-expressing.

The vacuum or other pressure source is preferably contained within the cushion, along with hoses or tubes (if needed) to one or more breast shields, and a container or containers for the expressed milk. The vacuum source may be battery-operated for portability, but can also be operated off of house current. The breast shield(s) are exposed or exposable (as by a removable cover or panel), on a soft cushioned or pillow-like surface, so the mother can hold/hug the pliable case to her chest, with her breast(s) inserted into the shield(s). The rest of the breastpump parts are essentially hidden within the cushion, in a most-preferred form of the invention.

The cushioned breastpump in one embodiment takes the form of a cushion having two breast shields, which are exposable on a generally planar soft surface. The mother hugs/holds the cushion to her chest, for double-pumping. The breast shields themselves could be formed in the cushion itself, with conduit structure, tubes, or the like extending to the integral breast shields. The breast shields could alternatively be made removeable (removeably mounted).

In another embodiment, the cushioned breastpump is adapted for single pumping, with one breast shield being exposed. This embodiment may further be somewhat elongated in form, like a papoose-shape. In this form, the inventive cushioned breastpump may be cradled like a baby at the breast, or in a "football" hold, with the breast shield located at or adjacent one end.

A strap or similar attachment device can be used for a "handsfree" version, or simply to facilitate holding the cushion in place.

The cushion in one form is preferably made to be opened to access the equipment within, such as for emptying the container(s), removing the breast shield(s) for cleaning, or to access a storage compartment that may be provided therein.

Shields aside, all of the rest of the breastpump equipment need not be completely hidden within the cushion. For instance, the milk container(s) and the conduit structure of the breastpump assembly could be located on the backside of the cushion, but exposed for ready access. Control elements may be located on the outside, or within an accessible compartment.

An embodiment of the cushioned breastpump has an element that is heatable, as in a microwave, which is then placeable within or on the cushion. Conversely, an element which is cooled or coolable may likewise be provided for placement in or on the cushion.

Other adaptations include a mount where a photograph of a baby may be placed for viewing in use. This could furthermore be a videoframe, with digital picture(s). A sound recording and playback apparatus can be provided within the cushion, which may be of soothing noise, music, a gurgling or cooing baby, and so forth (could be Metallica or ACDC, for that matter). A "scent" aspect may additionally be provided, including a pleasant baby smell, for one instance. Vibration may be advantageously employed, as for instance a pleasant thrumming, or a heartbeat-like movement, just to name two possibilities. Even a visual "glow" can be provided, for instance emanating within the cushion, that could be made rhythmic so as to mimic a baby's heartbeat.

The material of the cushion is preferably soft, at least where it comes in contact with the mother. It may be malleable, as for instance being made out of soft foam, so as to conform to the chest area for a more natural and comfortable feel. The cushion could be inflatable, or provided in an inflated form. It is most preferably cleanable, and may, for example, have a pillowcase-like enclosure which can be removed for cleaning. Materials generally used to make cushions, pillows, mattresses and the like are readily adaptable for use in the invention.

BRIEF DESCRIPTION OF THE DRAWINGS

These and other features and advantages of the present invention will be further understood and appreciated when considered in relation to the following detailed description of embodiments of the invention, taken in conjunction with the drawings, in which:

FIGS. 1a-1c show a cushioned breastpump according to certain aspects of the present invention;

FIG. 15 is a close-up view of an accessory of the cushioned breastpump shown in FIG. 14a;

DETAILED DESCRIPTION OF EMBODIMENTS OF THE INVENTION

Figure 2A:
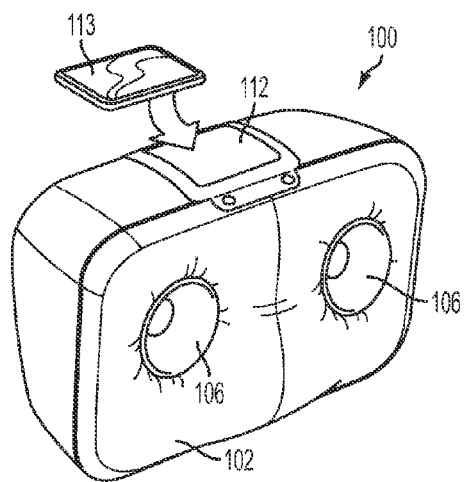
FIGS. 2a-2d are additional views of the cushioned breastpump similar to that shown in FIGS. 1a-1c.

One embodiment of the invention is a cushioned breastpump. Again, "cushion" is being used expansively to encompass all types of pillows, soft cases, blankets, pads, and the like. This type of breastpump is simply illustrative, and not intended to be limiting of the invention.

The cushioned breastpump 100 includes a cushion 102 made of a soft, malleable outer material, for at least partially enclosing a breastpump assembly 104 and associated accessories (tubing, collection container, etc.) The breastpump assembly 104 may include an electric pump, such as the pump disclosed in U.S. Pat. No. 6,547,756 or 6,257,847, each of which are incorporated herein by reference in their entirety, or may be battery powered, or use some other energy source (e.g., solar). The breastpump assembly 104 has one or more breast shields 106. This cushioned breastpump 100 also includes a flap 108 which opens to allow access to the breastpump equipment within the cushion. The breast shields 106 extend outwardly through holes 110 in the flap to receive a woman's breasts. Flap 108 is closed using a zipper 109, although many other types of closures will suffice (e.g., snaps, Velcro®, etc.)

Figure 2B:
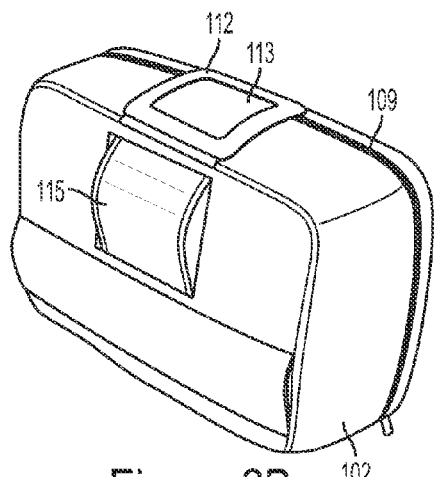
Figure 2C:
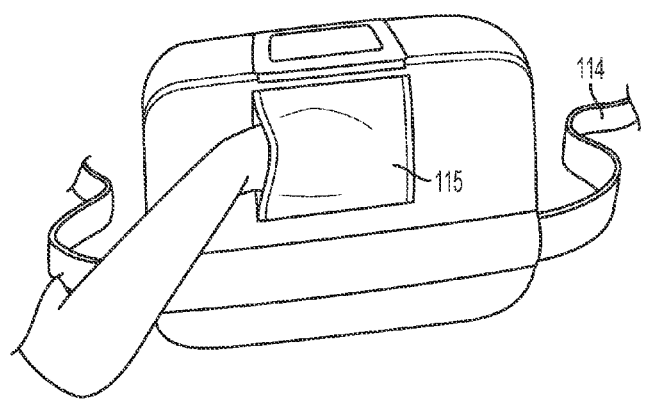
Figure 2D:
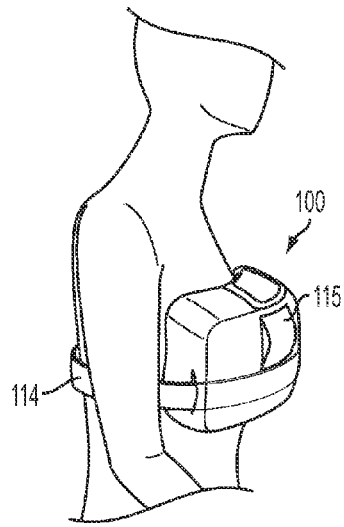

Referring now to FIGS. 2a and 2b, the cushion 102 may include at least one pocket or storage compartment 112 on an exterior surface, here in the form of a frame, as for a digital media device, photograph 113, or to store any other type of planar device on the cushion. Other compartments for storage of items can likewise be further provided. The cushion 102 may also include a strap 114 so the mother may attach the entire cushioned breastpump 100 to her body, for "hands-free" pumping, as shown in FIGS. 2c and 2d.

The embodiment shown in FIGS. 2a-2d also includes a packet or pouch 115 that mom can use to hold the cushion 102 in position. The pocket is accessible through either lateral side.

Figure 3C:
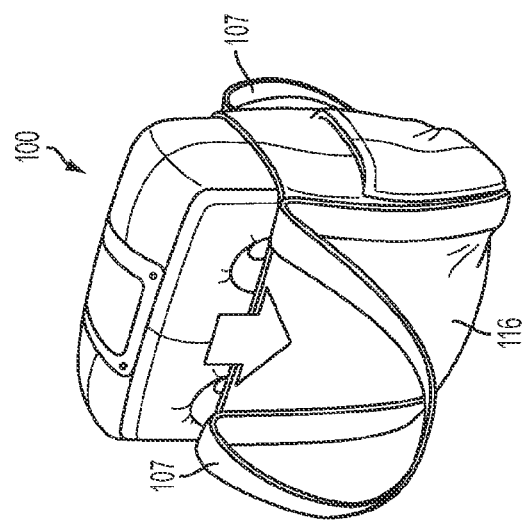
FIGS. 3a-3c show carrying cases for the cushioned breastpump.
Figure 3B:
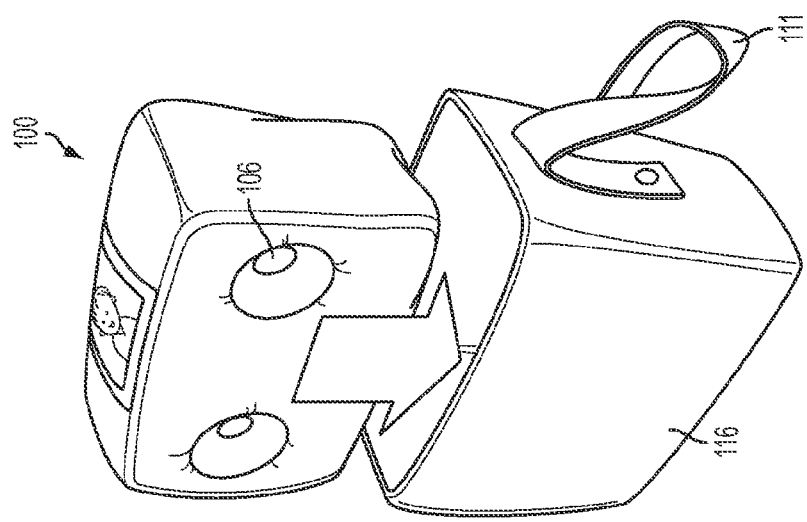
Figure 3A:
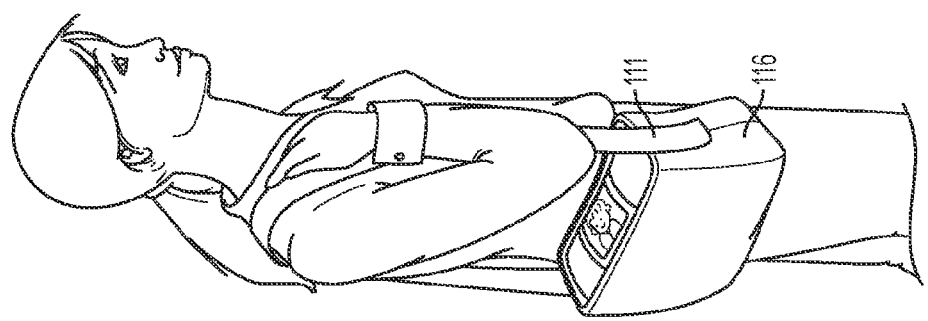
Figure 4:
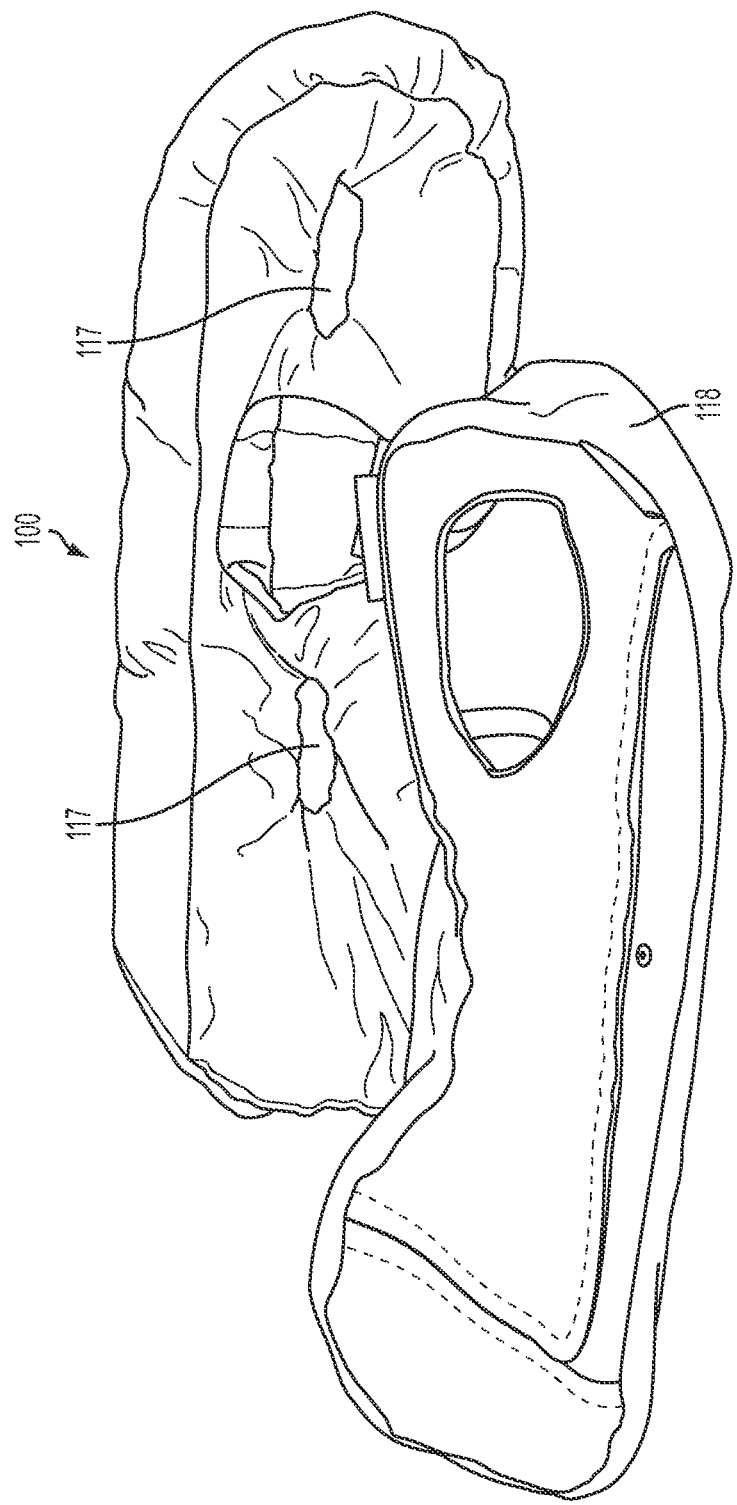
FIG. 4 shows an alternate embodiment of a cushioned breastpump.
Figure 5:
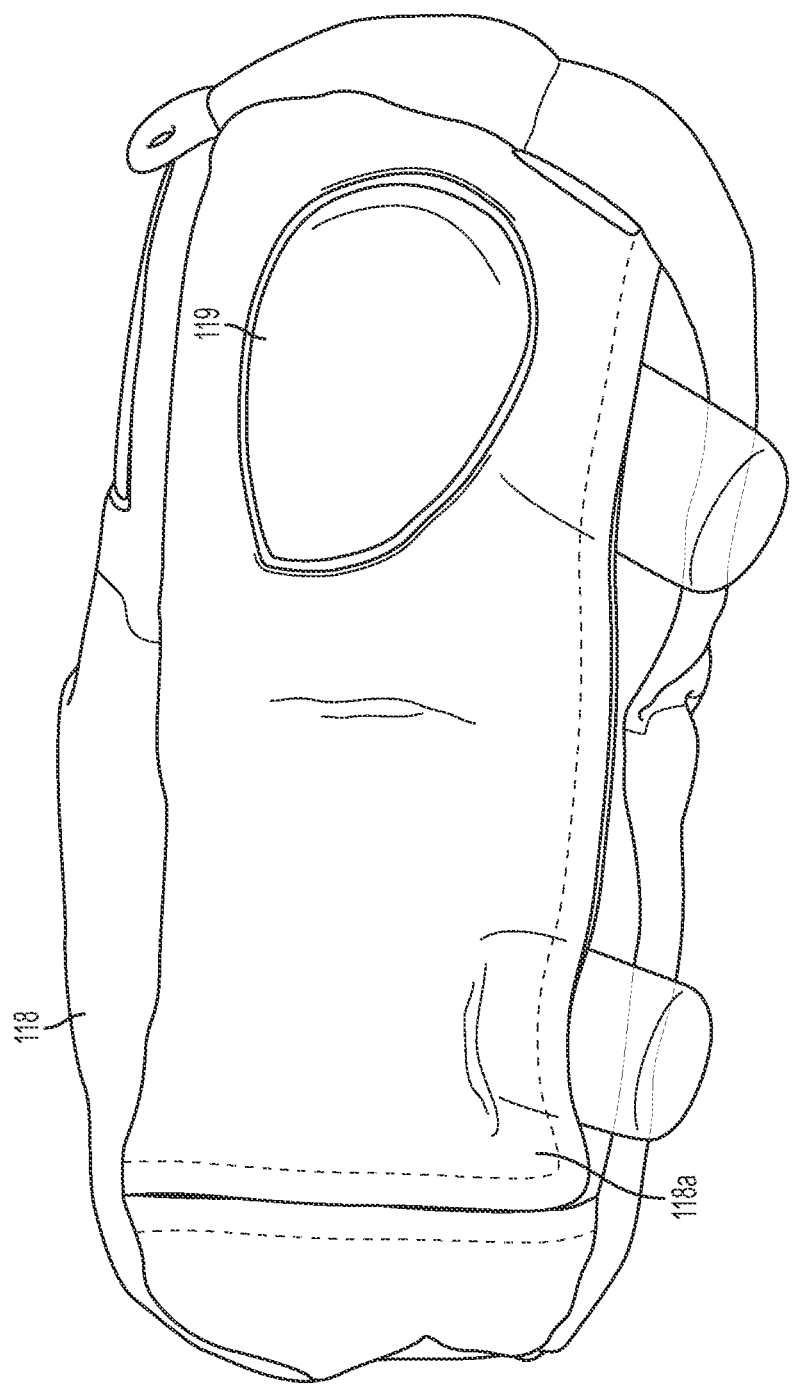
FIG. 5 shows a front view of the cushioned breastpump of FIG. 4.
Figure 6:
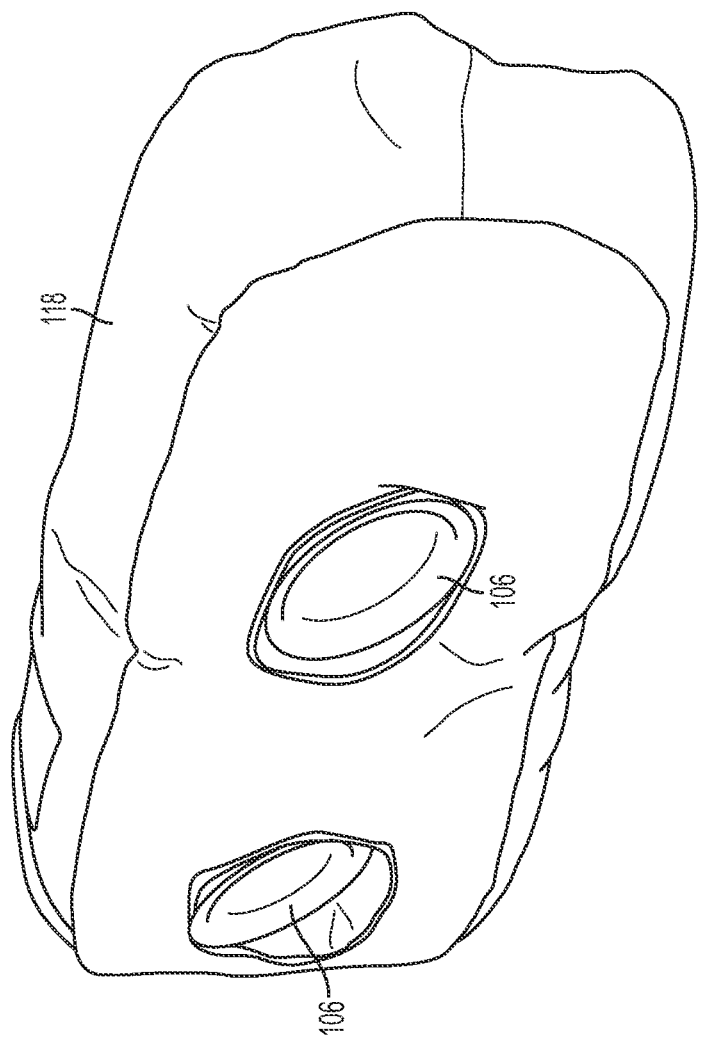
FIG. 6 shows a rear view of the cushioned breastpump of FIG. 4.
Figure 7:
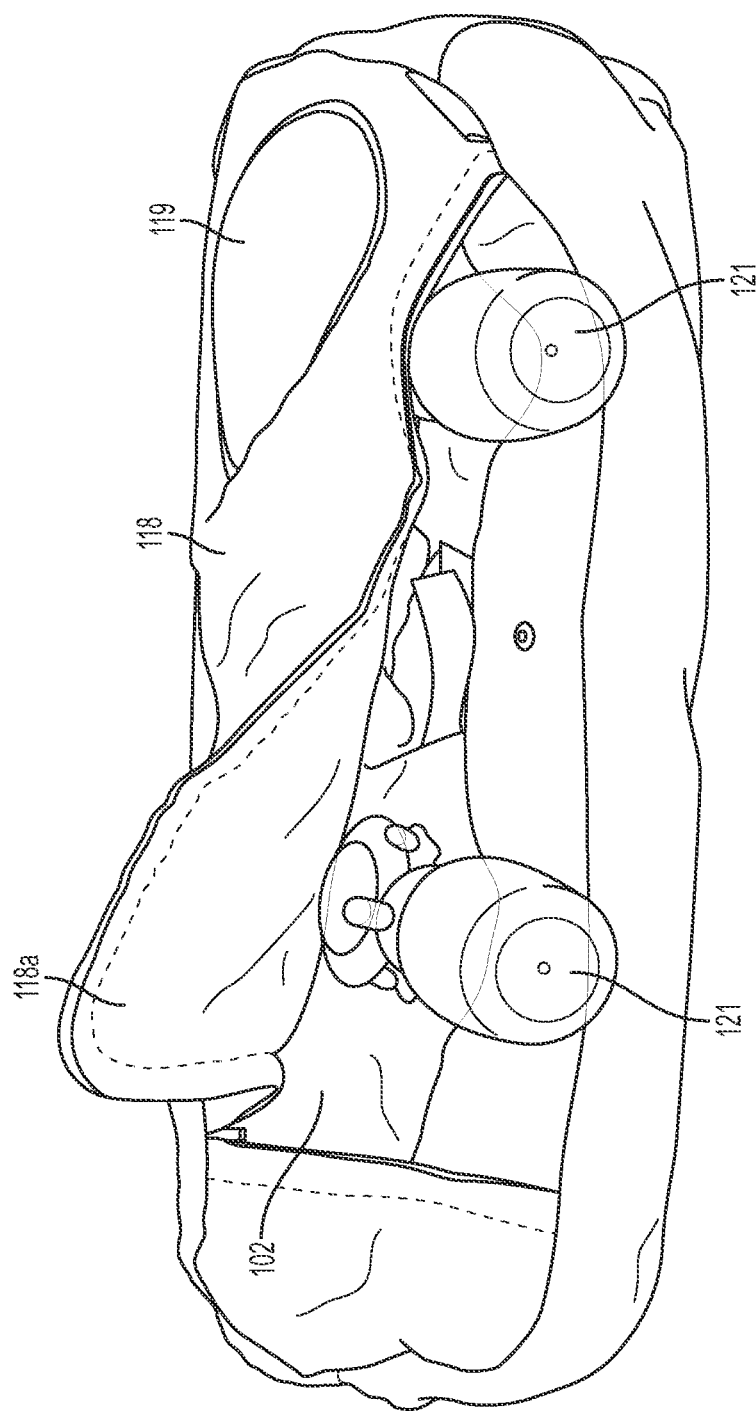
FIG. 7 shows an "open" view of the cushioned breastpump of FIG. 4.

The cushioned breastpump 100 may be stored in a carrying case 116, as shown in FIGS. 3a-3c, for easy storage or travel. FIGS. 3a and 3b have a shoulder strap 111; FIG. 3c has a pair of handles 107.

Figure 8:
FIG. 8 shows alternate designs for the cushioned breastpump of the present invention.

FIGS. 4-7 show the cushioned breastpump 100 including an outer sleeve 118. The outer sleeve may be removable, like a pillowcase, and may come in a number of different designs, as shown in FIG. 8. A vacuum pump 119 is shown in a compartment of the sleeve 118. Breast shields 106 (FIG. 6) extend into orifices 117 formed in the main cushion body 102. The rest of the breastpump assembly 104 and breastpump accessories can be seen in FIG. 7, such as collection containers 121. A flap 118a on the outer sleeve 118 closes them within the cushion 102, although the bottom of the containers is allowed to extend outside of the flap 118a.

Figure 9B:
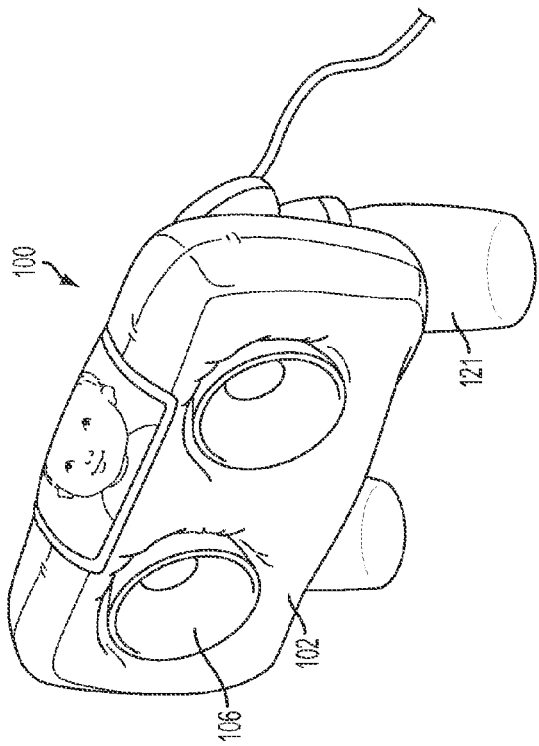
FIGS. 9a-9c show yet another embodiment of the cushioned breastpump of the present invention.
Figure 9C:
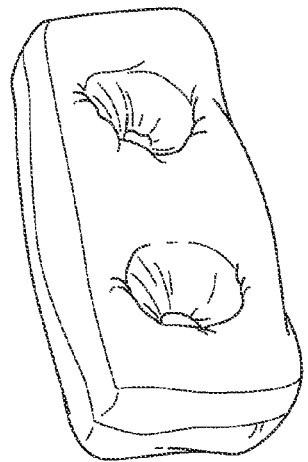
Figure 9A:
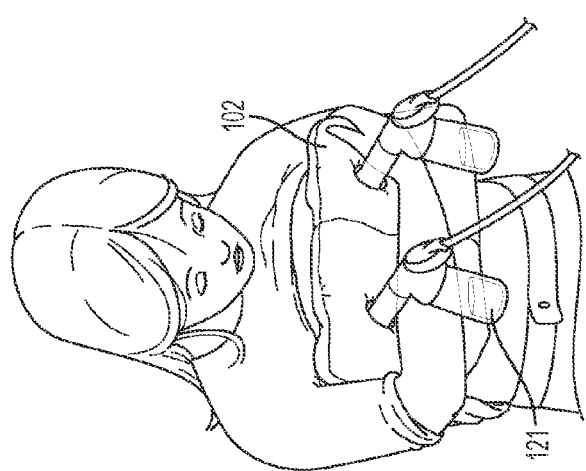

FIGS. 9a-9c show an alternate embodiment of the cushioned breastpump 100 in which the breastpump assembly 104 and associated accessories are not completely enclosed by the cushion 102. In this embodiment, collection containers 121 are located on the exterior of the cushion 102 and outer sleeve 118.

Figure 10B:
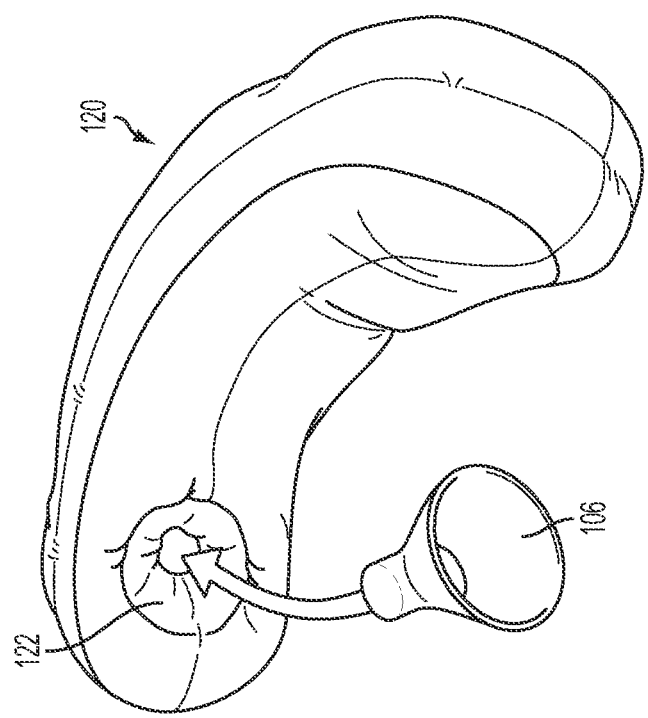
FIGS. 10a-10b show yet another embodiment of the cushioned breastpump of the present invention.
Figure 10A:
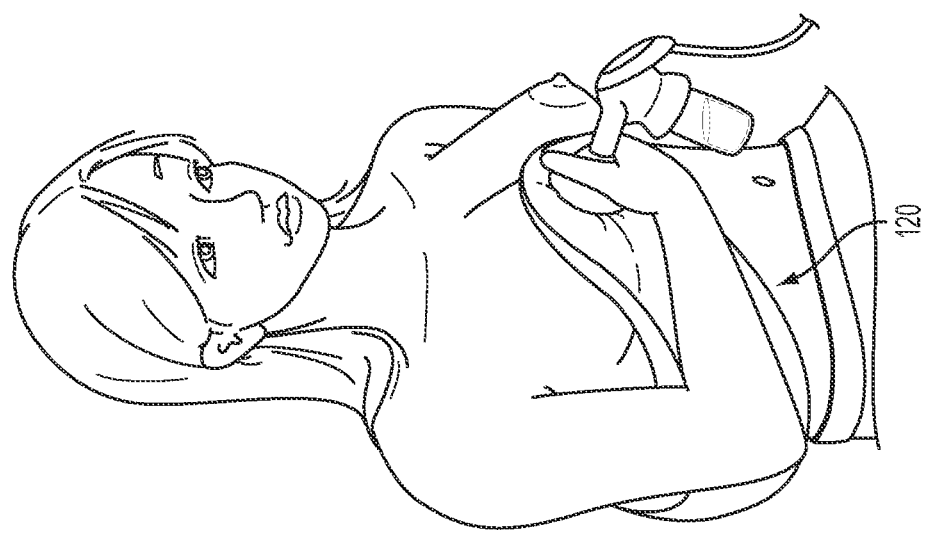
Figure 11C:
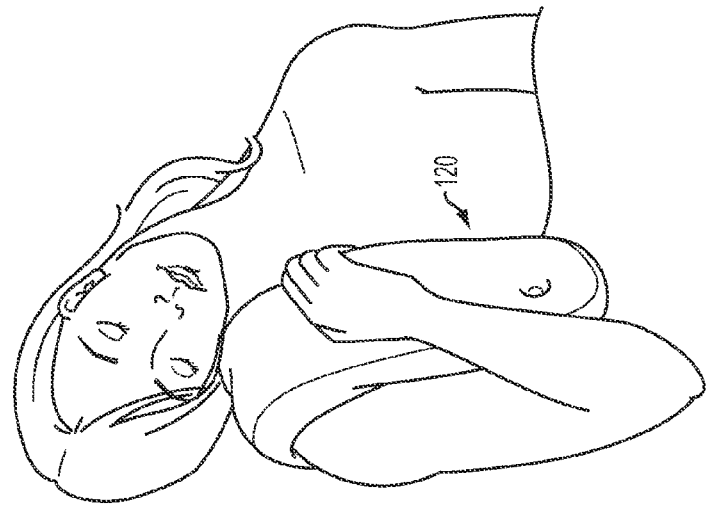
FIGS. 11a-11c show some alternate positions for using the cushioned breastpump shown in FIGS. 10a-10b.
Figure 11B:
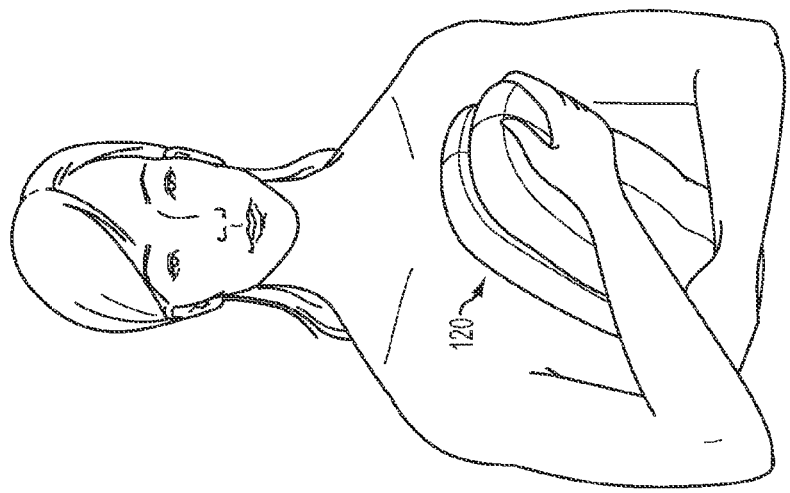
Figure 11A:
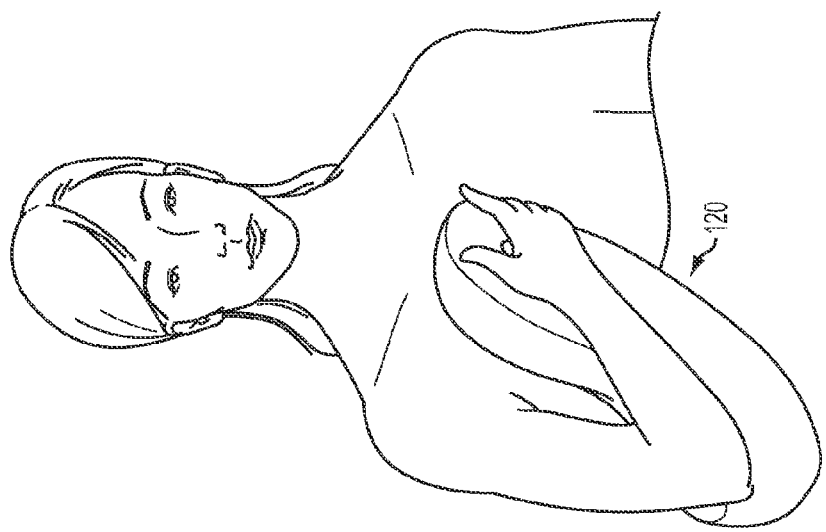

In yet another embodiment, shown in FIGS. 10a-10b, the cushioned breastpump may take an alternate shape, such as an elongated papoose-like shape 120. This shape may be more comfortable or desirable for some mothers. The elongated cushion 120 may include one hole 122 through which a breast shield 106 may be exposed. The elongated cushion 120 may be cradled like a baby at the breast, in a "football hold," or over the shoulder, as seen in FIGS. 11a-11c. It will be understood that the main pumping equipment previously described is contained within elongated cushion 120.

Figure 12A:
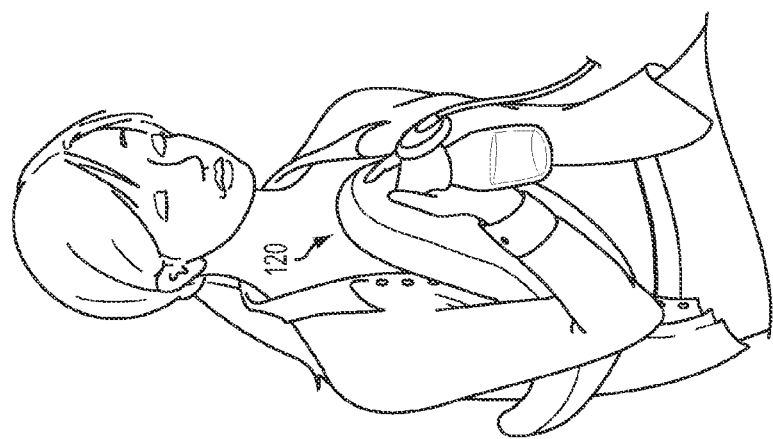
FIGS. 12a-12c show another embodiment of the cushioned breastpump of the present invention.
Figure 12B:
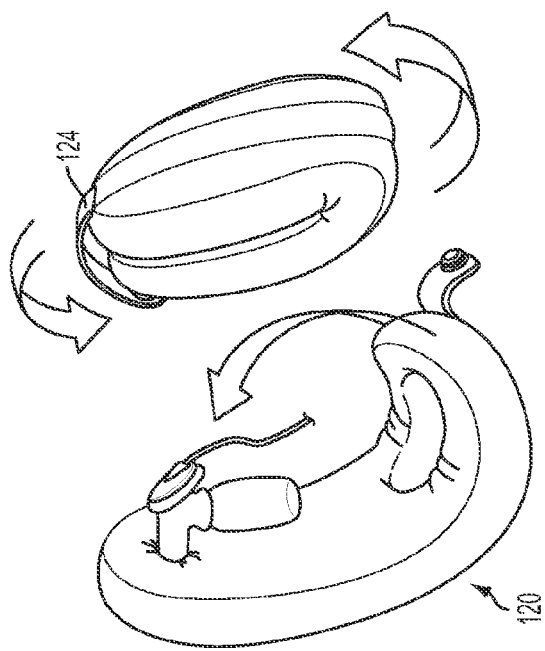
Figure 12C:
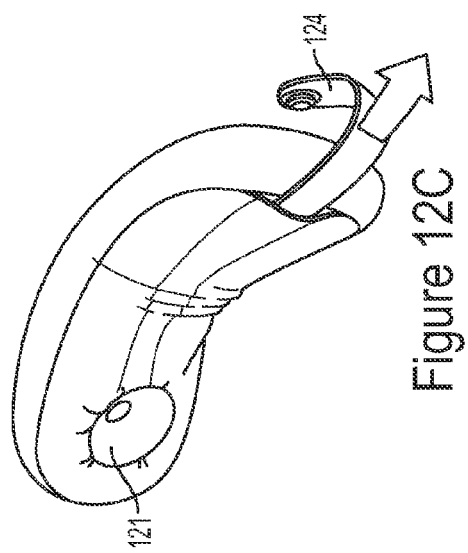

Referring to FIGS. 12a-12c, the elongated cushion 120 may further include a strap 124 which may be used to fold and store the cushioned breastpump when not in use, with a snap-attachment of the strap 124.

Figure 13A:
FIGS. 13a-13c are additional views of the cushioned breastpump shown in FIGS. 12a-12c.
Figure 13B:
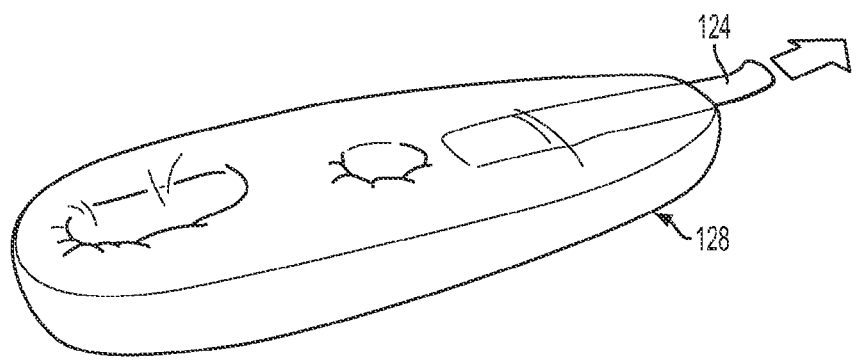
Figure 13C:
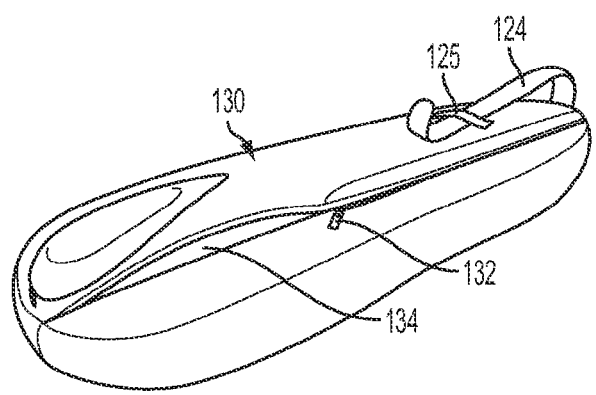
Figure 14A:
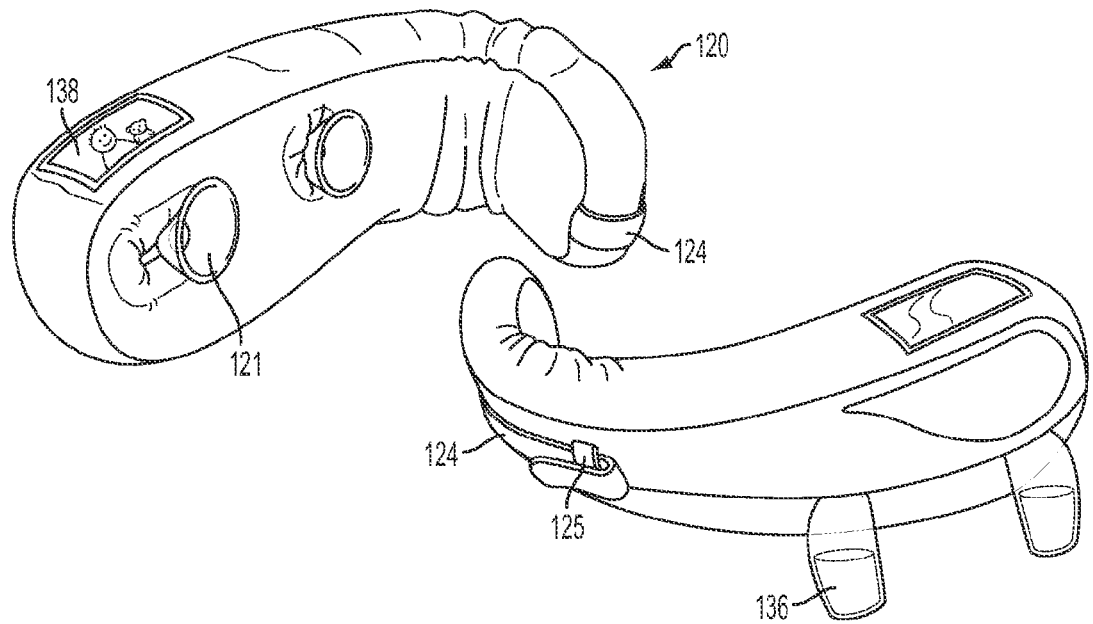
FIGS. 14a-14b show additional accessories that may be used with the cushioned breastpump of the present invention.

FIGS. 12c, 13c, and 14a show another use of strap 124. When the elongated cushion 120 is in use, the mother may pull on the strap 124 which curves the cushion to conform to her body. This may increase the comfort of the mother during pumping. The strap 124 is then folded around the cushion and pulled through loop 125 to hold it in place.

Figure 14B:
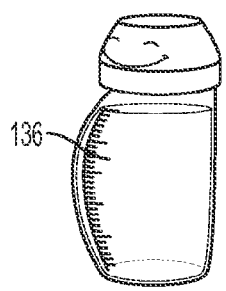

As shown in FIG. 13a, the elongated cushion 120 may include a water-resistant internal cushion 126 surrounding a breastpump (not shown). The elongated cushion 120 may also include a back cover 128, shown in FIG. 13b, and a front cover 130, shown in FIG. 13c, for surrounding the water-resistant cushion 126. The front cover 130 may include a hidden zipper 132 to allow access to an elongated opening 134 through which one or more collection containers 136 may extend (shown in FIGS. 14a and 14b). As best seen in FIG. 14b, the collection containers 136 may be in the form of a bottle having an outwardly protruding portion shaped like a baby's belly.

Figure 15:
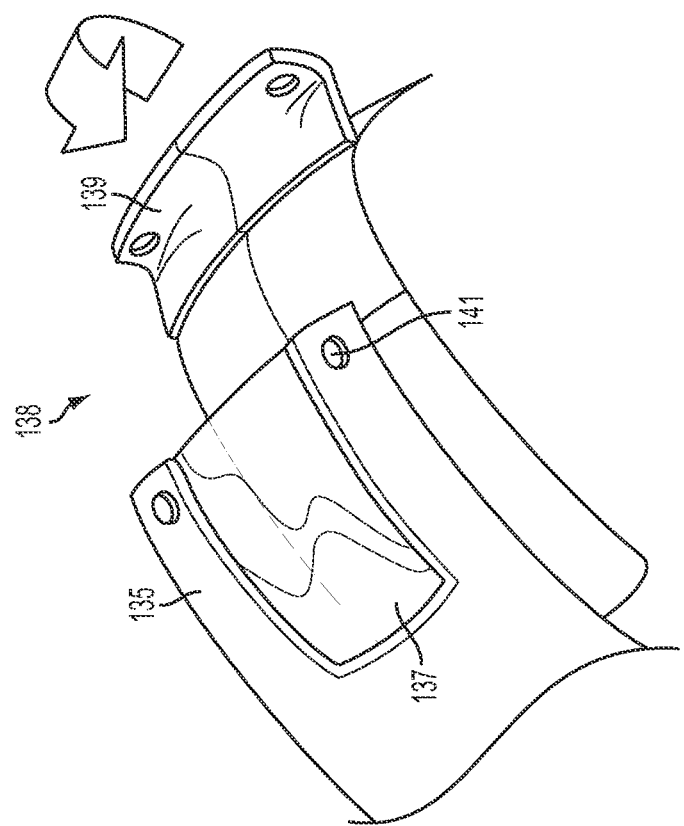

FIGS. 14-15 show different configurations of the elongated cushioned breastpump 120. As previously described, the cushioned breastpump may include a pocket or storage compartment 138 on an exterior surface for a digital media device, photograph, or to store any other type of device in the cushion.

FIG. 15 shows a close-up view of an example embodiment of the storage compartment 138. The storage compartment 138 may include a top flap 135 having a clear window 137 through which a photograph, digital media device, or other accessory can be seen. The storage compartment may further include a bottom flap 139 which can be folded over and fasten to the top flap 135 by fastener 141. One or more fasteners 141 may be used to secure the bottom flap 139 to the top flap 135 of the storage compartment 138. Suitable fasteners may include snaps, buttons, and hook and loop (Velcro®) fasteners, for example. Other possibilities exist as well.

Figure 16C:
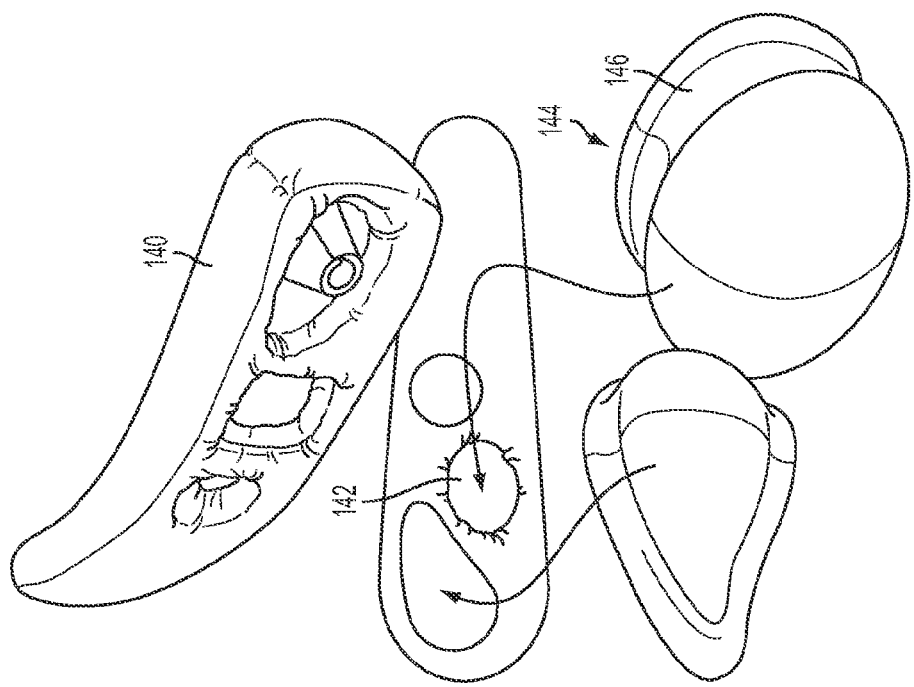
FIGS. 16a-16c show yet another embodiment of the cushioned breastpump of the present invention.
Figure 16A:
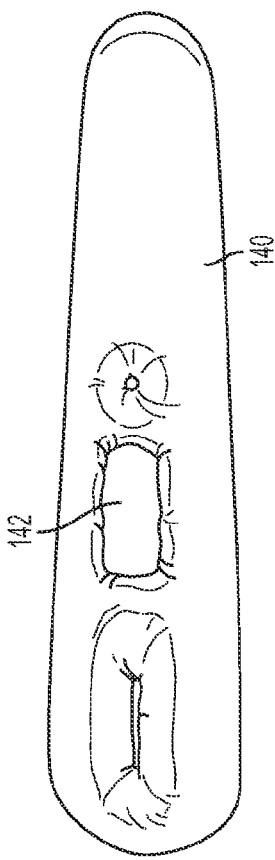
Figure 16B:
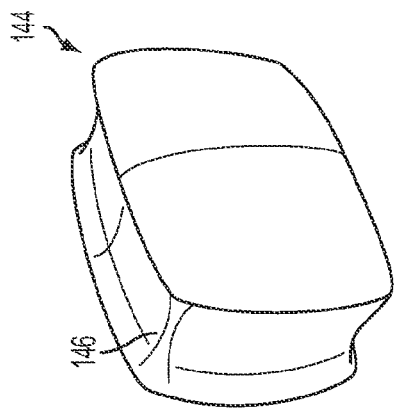

Referring to FIGS. 16a-16c, the elongated cushioned breastpump 120 may include an interior shell 140 having elastic-lined openings 142 for accommodating a motorized vacuum pump 144. The vacuum pump 144 may include an outer groove 146 to hold it in place in the elastic-lined openings 142. The pump 144 may take any number of shapes, such as rectangular or oval, as shown in FIGS. 15b and 15c.

Figure 17B:
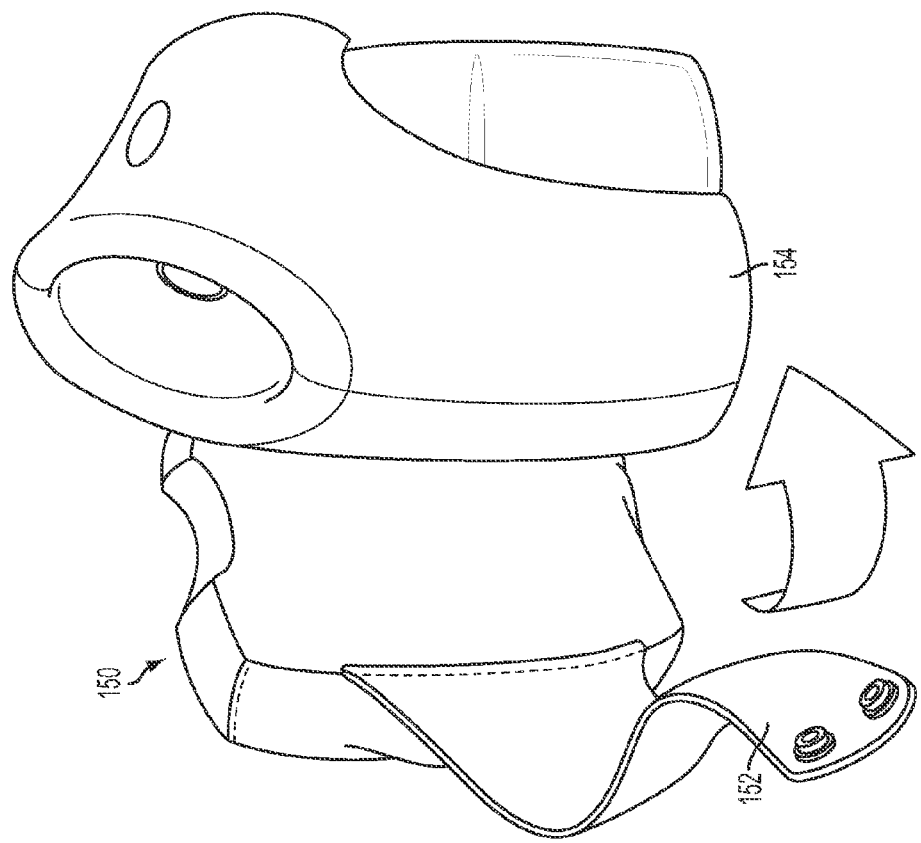
FIGS. 17a-17b show yet another embodiment of the cushioned breastpump of the present invention.
Figure 17A:
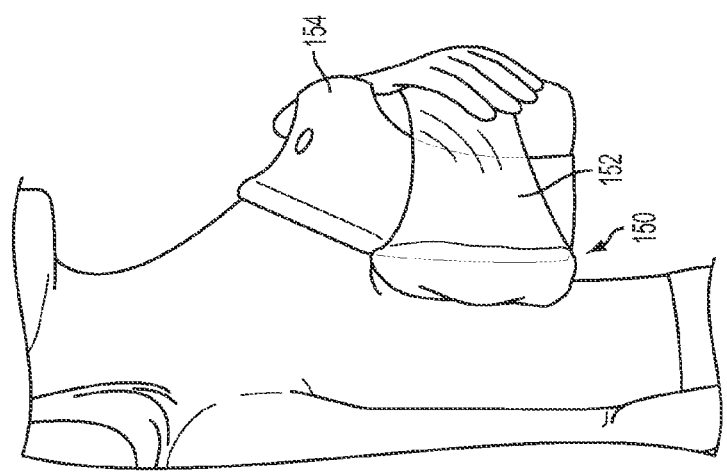

Referring to FIGS. 17a and 17b, another embodiment of a cushion is described. The cushion 150 includes a strap 152 for securing the cushion 150 to a breastpump assembly 154. Thus, the mother can remove the cushion 150 if desired. The cushion 150 may include a non-slip material for a secure fit on the breastpump assembly 154.

Any of the embodiments of the cushion described above may be heated, as by a separate element which can be warmed in a microwave and then attached to the cushion; or may contain a scent, such as "baby's breath" to give the mother a more relaxing and real experience.

Thus, while the invention has been described herein with relation to certain embodiments and applications, those with skill in this art will recognize changes, modifications, alterations and the like which still come within the spirit of the inventive concept, and such are intended to be included within the scope of the invention.

What is claimed is:

1. A breastpump carrier comprising:
   at least one breast shield within which a mother's breast is received;
   a soft, malleable housing which the mother can hold against her chest, said housing having an opening to insert said breast shield therein with said breast shield exposed on a side of said housing to receive a breast therein with said housing held against the mother's chest, wherein said housing is held in place by the mother's arm or hand.

2. The breastpump carrier of claim 1 wherein said breast shield is part of a breastpump assembly mounted at least partially within said housing.

3. The breastpump carrier of claim 1 wherein said breast shield is formed integral with said housing.

4. The breastpump carrier of claim 1 further comprising a motor-driven pressure pump, said pump providing pressure to said breast shield for the expression of milk, said pump being contained at least partially within said housing.

5. The breastpump carrier of claim 1 wherein two breast shields are provided for double-breast pumping.

6. The breastpump carrier of claim 1 wherein said housing is a cushion.

7. The breastpump carrier of claim 1 further including one or more of the following: a visual display for a picture; an aroma-generating medium; a light source visible through said base; a sound recording.

8. The breastpump carrier of claim 1 further wherein the housing comprises a water-resistant cushion placed within an outer sleeve.

9. The breastpump carrier of claim 1 wherein the housing has an elongated shape.

10. The breastpump carrier of claim 1 wherein the housing further comprises a storage compartment.

11. The breastpump carrier of claim 1 wherein the breast shield is exposable by a removable panel attached to the housing.

12. The breastpump carrier of claim 1 further comprising a collection container for receiving expressed milk, the collection container being located exterior to said housing.

13. The breastpump carrier of claim 12 wherein the collection container includes an outwardly protruding portion.

14. A breastpump carrier comprising:
   a soft housing having an extended surface which the mother can hold against her chest and sized to cover at least one breast and a substantial area surrounding the breast on the mother's chest;
   at least one breast shield within which a mother's breast is received;
   said housing having an opening to insert said breast shield therein with said breast shield exposed on said extended surface to receive a breast therein with said housing held against the mother's chest by the mother.

15. The breastpump carrier of claim 14 further comprising a pump providing pressure to said breast shield for the expression of milk, said pump being contained at least partially within said housing.

16. A breastpump comprising:
   at least one breast shield within which a mother's breast is received;
   a soft housing which the mother can hold against her chest, said housing having an opening to insert said breast shield therein with said breast shield exposed on a side of said housing to receive a breast therein with said housing held against the mother's chest and sized to cover a substantial area surrounding the breast on the mother's chest;
   a conduit structure contained within said housing conveying milk from said breast shield to a container, and conveying pressure from a pressure source to said breast shield for expressing milk; and
   a pressure source contained within said housing generating an intermittent pressure in said breast shield.

17. The breastpump of claim 16 wherein said housing covers a mother's torso with both breasts placed therein.

18. The breastpump of claim 17 further including a strap attached to said housing, said strap extending around a mother's back to thereby affix said housing to the mother in a hands-free arrangement.

19. The breastpump of claim 18 further including one or more of the following: a visual display for a picture; an aroma-generating medium; a light source visible through said base; a sound recording.

20. A breastpump carrier comprising:
   at least one breast shield within which a mother's breast is received;
   a soft housing having an elongated shape which the mother can hold against her chest, said housing having an opening to insert said breast shield therein with said breast shield exposed on a side of said housing to receive a breast therein with said housing held against the mother's chest; and
   a pump providing pressure to said breast shield for the expression of milk, said pump being contained at least partially within said housing.

21. The breastpump carrier of claim 20 wherein the housing includes a strap.

22. The breastpump carrier of claim 20 wherein the housing is a cushion.

* * * * *